May 5, 1942. R. L. BYRUM Plant Pat. 513
ROSE PLANT
Filed Oct. 29, 1941
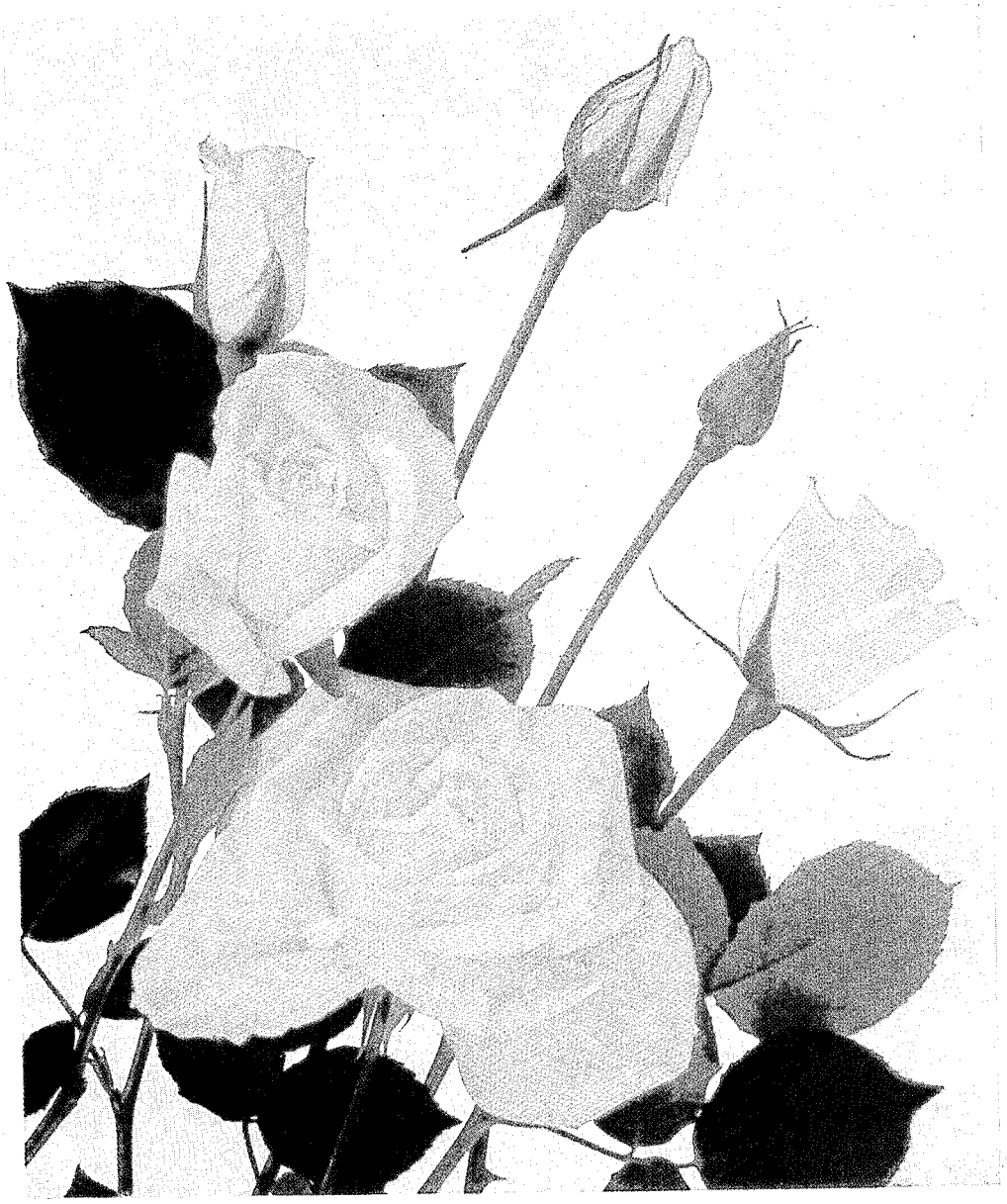
Inventor
R. L. Byrum
By Robb & Robb
Attorneys Patented May 5, 1942

Plant Pat. 513

UNITED STATES PATENT OFFICE

513

ROSE PLANT

Roy L. Byrum, Richmond, Ind., assignor to Joseph H. Hill Company, Richmond, Ind., a corporation of Indiana Application October 29, 1941, Serial No. 417,045

1 Claim. (Cl. 47—61)

The present invention relates to a new and distinct variety of hybrid tea rose plant, originating as a result of efforts to obtain a rose in the pink color range improving upon the rose "Ophelia," and progeny including "Rapture," as regards certain of their undesirable characteristics.

To this end, I crossed the variety "Ophelia" with an unnamed seedling and thereby produced the new rose hereinafter more specifically described.

Having reference to its primary characteristics, this new rose is very productive and in form is like "Rapture," but it produces longer canes; in respect to color, it is more vivid than "Rapture"; and finally its bud is longer and it does not have the bending peduncle which is characteristic of "Rapture."

The various characteristics of this new rose are set forth in the following detail description, color terminology being in accord with Ridgway's Color Standard and with general dictionary terms:

Type: Bush; greenhouse; seedling; for cut flowers.

Class: Hybrid Tea.

Breeding or discovery: Seedling.

*Seed parent.*—"Ophelia."

*Pollen parent.*—Unnamed seedling, a thornless red rose produced by crossing a sport of "Premier" and "E. G. Hill."

Propagation: Holds its distinguishing characteristics through succeeding propagations by cutting, grafting and budding.

*Flower*

Locality where grown: Richmond, Indiana.

Flowers borne: Singly to stem; on normal, medium length stems.

Quantity of bloom: Abundant in greenhouse.

Continuity: Continuous.

Fragrance: Strong; tea.

Bud: Medium length; medium heavy; erect; stiff; green; entirely smooth; few green hairs.

*Before calyx breaks.*—*Size* — medium. *Form*—short; pointed; globular; with a conspicuous neck; with foliaceous appendages on the surface of the bud; with much-cut, foliaceous parts extending beyond the tip of the bud equal to three-fourths or more of its length.

*As calyx breaks.* — *Color* — base — Apricot Buff, Plate XIV, shading into Eugenia Red, Plate XIII.

*As first petal opens.*—*Size*—medium. *Form*—long; pointed. *Color*: Outside, Base—Apricot Buff, Plate XIV, shading Deep Rose Pink, Plate XII; inside—Apricot Buff, Plate XIV, streaked with Deep Rose Pink, Plate XII, instead of smooth. Opening—opens up well.

Bloom:

*Size when fully open.*—Medium; four inches to four and one-half inches.

*Petalage.*—Double; from twenty-five to thirty petals; arranged irregularly.

*Form.*—Open; high center at first, becoming open; Petals remaining at first loosely rolled outward; becoming later, at maturity, very loosely rolled outward.

Petals: Thick; soft; with inside and outside satiny.

*Shape.*—Outside—obovate; apex flat with one notch. Intermediate—obovate; with apex flat with one notch. Inside—obovate; with apex flat with one notch.

This description of a newly opened flower was made from a rose grown in a greenhouse in the month of September, 1941, at Richmond, Indiana:

*Color.*—Outside petal: outside surface—Cameo Pink, Plate XXVI, tinted with Thulite Pink, Plate XXVI; inside surface—White penciled with Pale Vinaceous, Plate XXVII. Intermediate petal: outside surface—Cameo Pink, Plate XXVI, tinted with more Thulite Pink, Plate XXVI; inside surface—White penciled with Livid Pink, Plate XXVII. Inner petal: outside surface—Thulite Pink, Plate XXVI, edged with Spinel Pink, Plate XXVI; base Apricot Buff, Plate XIV; inside surface—White penciled with Livid Pink, Plate XXVII.

This description was made from a rose that was open for three days in a greenhouse in the month of September, 1941:

*Color.*—Outside petal: outside surface—Cameo Pink, Plate XXVI, tinted with Thulite Pink, Plate XXVI; inside surface—Pale Vinaceous, Plate XXVII. Inside petal: outside surface—Cameo Pink, Plate XXVI; inside surface—Pale Vinaceous, Plate XXVII.

*General color effect.*—Newly opened flower—Thulite Pink, Plate XXVI. Three days open—Cameo Pink, Plate XXVI.

*Behavior.*—Persist.

*Flower longevity.*—Cut roses grown in greenhouse kept at living room temperatures five days in September.

*Reproductive organs*

Stamens: Many, arranged regularly about pistils.
Filaments: Long; yellow; most with anthers.
Anthers: Small; reddish brown; all open at once.
Pollen: Abundant; gold.
Pistils: Many.
Styles: Uneven; medium length; medium heavy; bunched.
Stigma: White.
Ovaries: Some protruding from calyx.
Sepals: Permanent; moderately short; curled.

*Color.*—Inside—Light Bice Green, Plate XVII, overlaid with white fuzz; outside—Light Bice Green, Plate XVII.

*Plant*

Foliage:

*Leaves.*—Compound of five leaflets; very abundant; medium large; heavy; wrinkled.

*Leaflets.*—Ovoid with apex acute; base obtuse; margin simply serrate.

*Color.*—*Mature*: upper surface — Dark Green; under surface—Very Light Green. *Young*: upper surface—Green Bronze Red; under surface—Bronze Red.

*Rachis.*—Light: upper side—grooved; hairy under side—smooth; prickly.

*Stipules.*—Short; medium width; with long points turning out at an angle of less than 45°.

*Disease.*—Resistant to mildew and blackspot.

Growth:

*Habit.*—Bush; upright; much branched.

*Growth.*—Free; vigorous.

*Canes.*—Medium heavy.

*Main stems.*—Bright Green. *Thorns*—few; medium length; hooked downward; with short, narrow base. *Prickles*—few; Red. *Hairs*—none.

*Branches.*—Bright Green. *Thorns*—few; medium length; hooked downward; with short, narrow base. *Prickles*—few; reddish. *Hairs*—none.

*New Shoots.*—Dull Bronze Red. *Thorns*—few; medium length; hooked downward; with short, narrow base. *Prickles*—few; reddish. *Hairs*—none.

I claim:

A new and distinct variety of hybrid tea rose plant, characterized as to novelty by its form and long canes, by the stiffly erect peduncle, and great productivity, and by the long bud and vivid coloring of its flowers, substantially as shown and described.

ROY L. BYRUM.